(12) United States Patent
Sunkel et al.

(10) Patent No.: US 9,713,580 B2
(45) Date of Patent: Jul. 25, 2017

(54) DEVICE FOR APPLYING A COSMETIC COMPOSITION

(71) Applicant: The Procter & Gamble Company, Cincinnati, OH (US)

(72) Inventors: Jorge Max Sunkel, Cincinnati, OH (US); Karen Kay Kalla, Cincinnati, OH (US); Larry Wayne Marshall, Jr., Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/688,051

(22) Filed: Apr. 16, 2015

(65) Prior Publication Data

US 2015/0297471 A1    Oct. 22, 2015

Related U.S. Application Data

(60) Provisional application No. 61/980,410, filed on Apr. 16, 2014.

(51) Int. Cl.
*A61K 8/02* (2006.01)
*A61Q 1/02* (2006.01)

(52) U.S. Cl.
CPC .......... *A61K 8/0216* (2013.01); *A61K 8/0208* (2013.01); *A61Q 1/02* (2013.01); *A61K 2800/87* (2013.01)

(58) Field of Classification Search
CPC ................ A61K 8/0216; A61K 8/0208; A61K 2800/87; A61Q 1/02
See application file for complete search history.

(56) References Cited

U.S. PATENT DOCUMENTS

| | | | |
|---|---|---|---|
| 4,169,169 | A | 9/1979 | Kitabatake |
| 5,078,160 | A | 1/1992 | Carbonnier |
| 5,137,040 | A | 8/1992 | Iosilevich |
| 5,691,020 | A | 11/1997 | Kondoh |
| 5,962,110 | A | 10/1999 | Penke-Wevelhoff |
| 6,074,721 | A | 6/2000 | Moore |
| 6,197,420 | B1 | 3/2001 | Takamizawa |
| 6,207,874 | B1 | 3/2001 | Felton |

(Continued)

FOREIGN PATENT DOCUMENTS

| | | |
|---|---|---|
| EP | 0 953 460 A2 | 11/1999 |
| EP | 1 167 072 A1 | 1/2002 |

(Continued)

OTHER PUBLICATIONS

International Search Report and Written Opinion of the International Searching Authority mailed Jul. 9, 2015, PCT/US2015/026056, 11 pages.

(Continued)

*Primary Examiner* — Trevor Love
(74) *Attorney, Agent, or Firm* — John G. Powell

(57) ABSTRACT

A cosmetic applicator for providing a natural looking cosmetic benefit. The cosmetic applicator includes a substrate and a solid, transferrable cosmetic composition disposed on the substrate. The cosmetic composition is configured as a multitude of dots arranged in a discontinuous stochastic pattern. The cosmetic composition comprises a colorant and an adhesive and in some instances has an L* value of from about 30 to 80, a c* value of from about 15 to 50, and an h* value of from about 30 to 80.

14 Claims, 5 Drawing Sheets

(56) References Cited

U.S. PATENT DOCUMENTS

| | | |
|---|---|---|
| 6,264,786 B1 | 7/2001 | Cromett |
| 6,461,626 B1 | 10/2002 | Rabe |
| 6,514,504 B1 | 2/2003 | Yen |
| 6,558,682 B2 | 5/2003 | Yen |
| 7,517,571 B2 | 4/2009 | Funke |
| 7,892,627 B2 | 2/2011 | Doughty |
| 2002/0110672 A1 | 8/2002 | Muratore-Pallatino |
| 2002/0182384 A1 | 12/2002 | Rhein |
| 2004/0037858 A1 | 2/2004 | Mammone |
| 2006/0013844 A1 | 1/2006 | Meriaux |
| 2008/0206373 A1 | 8/2008 | Millikin |
| 2009/0032053 A1 | 2/2009 | Griffiths |
| 2009/0032054 A1 | 2/2009 | Griffiths et al. |
| 2010/0189669 A1 | 7/2010 | Hakozaki |
| 2010/0239619 A1 | 9/2010 | Hurwitz |

FOREIGN PATENT DOCUMENTS

| | | |
|---|---|---|
| FR | 2 792 192 | 10/2000 |
| JP | 2001-278739 A | 10/2001 |
| WO | WO 99/61234 A1 | 12/1999 |
| WO | WO 02/36363 A1 | 5/2002 |
| WO | WO 02/36364 A3 | 5/2002 |
| WO | WO 2006/128737 | 12/2006 |
| WO | WO 2006/138723 A2 | 12/2006 |
| WO | WO 2008/090496 | 7/2008 |
| WO | WO 2010/086901 A1 | 8/2010 |
| WO | WO 2010/146570 A2 | 12/2010 |
| WO | WO2011/064719 A1 | 6/2011 |
| WO | WO 2013/093889 | 6/2013 |

OTHER PUBLICATIONS

Mintel Gnpd Eye Tattoo Exotic Eye Shadow Appliqués Record Id: 1441681 Nov. 2010.

Mintel Gnpd Temporary Lip Tattoos Record ID: 1736646 Feb. 2012.

Mintel Group Ltd., Category Insight: Body Colour Cosmetics, Mar. 2012, 57 pages.

DEVICE FOR APPLYING A COSMETIC COMPOSITION

FIELD OF THE INVENTION

The present application is directed, generally, to an applicator for applying a cosmetic composition to a target surface. More specifically, the present application discloses an applicator for applying a natural looking cosmetic composition to skin in the form of a multitude of dots arranged in a discontinuous stochastic pattern.

BACKGROUND OF THE INVENTION

A wide variety of cosmetic compositions have been in use for many years to emphasize features or to hide perceived blemishes, and a wide range of application methods are known for applying such compositions. While most cosmetics users want to hide perceived skin blemishes, some do not want the treated area to appear as though makeup has been applied. In other words, these users desire good cosmetic coverage, but with a natural look. Thus, there is a need for improved cosmetic applicators and application methods that consistently provide good coverage while maintaining a natural look.

One approach to providing a consistent cosmetic benefit is to print a pattern onto a substrate, which can then be placed on a target skin surface in a semi-permanent fashion. The substrate is generally transparent so that a user can more precisely place the pre-printed pattern on a desired skin location and the pattern is visible thru the substrate. This approach is commonly used for the application of so-called temporary tattoos. Conventional temporary tattoo devices typically include an image printed onto a film material using, for example, a conventional printing process and FDA-certified ink. The image and/or the substrate may also include an adhesive, which keeps the image-containing substrate in place on the skin. While temporary tattoo devices may be suitable for consistently providing a noticeable, long-lasting cosmetic benefit, they are generally not suited for providing a natural look on skin. For example, the image-containing film that is adhered to the skin may cause the skin to have an undesirable "shiny" appearance. In addition, the edges of the film may form lines that are easily detected by the human eye. Skin-colored films and feathered printing techniques have been developed to reduce the unsightliness of the transparent films, but even with these changes the image-containing film is still susceptible to undesirable physical deformation such as wrinkling caused by the stretching and/or relaxing of a user's skin. These sorts of physical deformations can be readily detected by the human eye and may detract from a natural look. In addition, the film may provide an undesirable feel on the skin of a user. Examples of temporary tattoos as well as other similar products that utilize a film substrate adhered to the skin are disclosed in U.S. Pat. Nos. 5,962,110, 6,074,721, 6,197,420, 6,207,874, 6,264,786 and 7,517,571; U.S. Publication Nos. 2002/01100672 and 2006/0013844; and PCT Publication Nos. WO 2006/128737 and WO 2010/086901.

To overcome some of the problems associated with using printed films, "pre-loaded" applicators have been developed. Examples of conventional pre-loaded applicators can be found in U.S. Pat. Nos. 4,169,169 and 5,078,160; and U.S. Publication Nos. 2004/0037858 and 2009/0032053.

Conventional pre-loaded applicators typically include a transferable composition (e.g., ink or a conventional cosmetic composition) disposed on a substrate such as a polyethylene film. A user can contact the composition-containing portion of the substrate with a target skin surface to transfer at least some of the composition to the skin and then dispose of or recycle the applicator. It is not uncommon for the composition to be in the form of an FDA-approved ink or a dry powder, which can be transferred to the skin because the composition has a greater affinity for skin than it does for the applicator substrate. Similarly, the composition may be held in place on the skin because of its affinity for the skin. One drawback to this approach is that a variety of factors may impact the transfer of the composition and/or how long the composition remains on the skin, which impacts how consistently and/or how long the cosmetic benefit can be provided. Such factors include the force applied during transfer, the condition of the skin (e.g., oily or dry); the type of cosmetic agent (e.g., particles size, particle shape, hydrophilicity/hydrophobicity); environmental conditions (e.g., humid or dry).

To mitigate the variability in consistency and longevity of the cosmetic benefit provided by a pre-loaded applicator, an excess amount of cosmetic composition may be provided on the substrate to ensure that at least a minimum amount is transferred to the target surface. But providing excess composition on the substrate still might not suitably reduce the variability in how much composition is transferred to the skin and/or how long the cosmetic benefit lasts. Additionally, providing excess composition on the substrate is not efficient or cost effective.

To address the variability in cosmetic application associated with conventional pre-loaded applicators, a two-step system has been developed. An example of such a two-step system is disclosed in PCT Publication No. WO2011/064719. In a conventional two-step system, an adhesive may be transferred from a first applicator to a target skin surface in the form of continuous or discontinuous adhesive film. Application of the adhesive film layer is then followed by application of a cosmetic agent (e.g., colorant particles) from a second applicator. The cosmetic agent is held to the target skin surface by the adhesive. In this way, the cosmetic agent can be applied only to areas where the adhesive is present, which may reduce the variability in the amount of cosmetic delivered to the target skin surface. However, the two-step system has drawbacks of its own. One drawback is the inconvenience of a two-step process. At least some, if not most, users prefer the convenience of a one-step system. In addition, a two-step system may still introduce some variability in how the applied cosmetic appears, for example, depending on how a user positions the applicators during application and/or how readily the cosmetic agent is transferred from the applicator to the target surface. Further, the pattern formed by the applied cosmetic composition may result in a cosmetic benefit that does not look natural, especially when the adhesive is applied as a uniformly distributed, discontinuous film. Uniformly distributed patterns are generally not found naturally on the skin, and thus may be readily detected by the human eye when present.

Another attempt at consistently providing a natural looking cosmetic benefit involves the use of electrostatic spraying systems. Examples of electrostatic spraying systems are disclosed in U.S. Pat. Nos. 6,461,626 and 6,514,504. Electrostatic spraying typically involves raising the electric potential of the cosmetic composition to a high level in a spray nozzle such that the composition is atomized as a spray of electrically charged droplets. The electrically charged droplets seek the closest earthed object to discharge their electric charge, which is typically a target skin surface, resulting in the formation of a uniform, discontinuous film of cosmetic composition on the target surface. The uniform, discontinuous film formed on the skin allows a portion of the user's skin to be integrated into the overall appearance of the product application, which may result in a more natural look and may allow for broader useful shade palettes. However, electrostatic spraying lacks the convenience of a pre-loaded applicator system. In particular, electrostatic spraying may require the use of a specialized apparatus, a conductive composition, and/or a trained or experienced user to apply the composition. In addition, the uniformity of the applied composition may still undesirably impact how natural the cosmetic benefit is perceived, for example, by producing noticeable edges. As with the two-step pre-loaded applicator, uniform patterns can be readily detected by the human eye.

Accordingly, it would be desirable to provide a pre-loaded cosmetic applicator that enables a user to conveniently apply a cosmetic composition and consistently achieve a natural looking cosmetic benefit.

SUMMARY OF THE INVENTION

Figure 1:
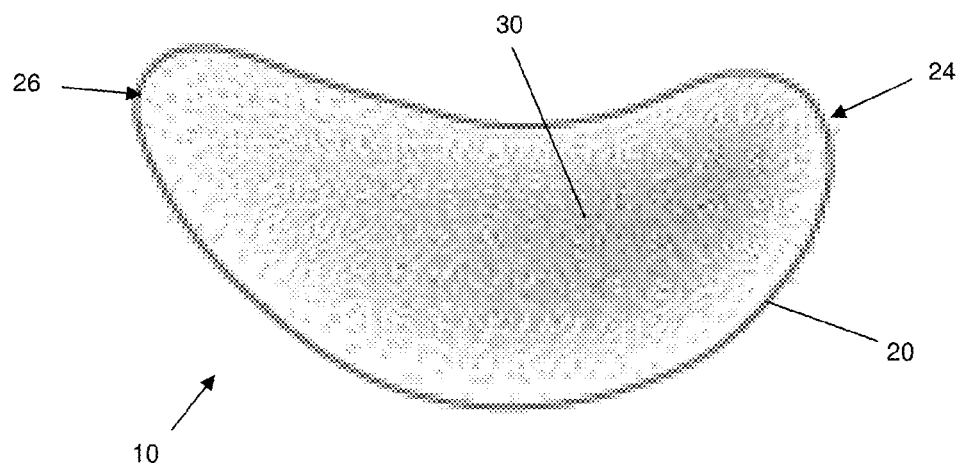
FIG. 1 is a plan view of a cosmetic applicator.

In some aspects, disclosed herein is a cosmetic applicator for providing a natural looking cosmetic benefit, comprising. The cosmetic applicator comprises a substrate and a solid, transferable cosmetic composition disposed on the substrate. The cosmetic composition is configured as a multitude of dots arranged in a discontinuous stochastic pattern. The cosmetic composition comprises a colorant and an adhesive and has an L* value of from about 30 to 80, a c* value of from about 10 to 50, and an h* value of from about 30 to 80. In some instances, the cosmetic applicator may include one or more of the following in any combination: dots having a contrast ratio of between about 0.1 and 0.6; dots having a maximum dimension of between about 10 µm and 250 µm; dots having a radius ratio of between 1 and 10; at least a portion of one surface of the applicator having an area of coverage of the cosmetic composition of from about 10 to 50%; a first portion of the applicator having a first area of coverage and a second portion of the application having a second area of coverage, wherein the first area of coverage is greater than the second area of coverage or at least 50% greater; a second portion of the applicator circumscribing a first portion; a pattern of dots comprising a diffuse edge; a substrate formed from a pliable foam material; the applicator being shaped to conform to a periorbital region of a human face; the substrate including a release layer and the cosmetic composition is disposed on the release layer; a release layer having a surface energy of between about 18 and 30 dynes/cm; the cosmetic composition including more than one colorant; the colorant being a plurality of pigment particles dispersed in the adhesive; a ratio of pigment to adhesive in the composition being from about 1:10 to 1:1.

Also disclosed herein is a cosmetic applicator comprising a substrate configured to support a transferable cosmetic composition and a solid, transferable cosmetic composition disposed on the substrate as a multitude of dots arranged in a discontinuous stochastic pattern. The cosmetic composition comprises a colorant and an adhesive and the composition provides a Color Improvement Value of at least about 1% and a ΔE of less than about 10 when applied to a target skin surface comprising periorbital dyschromia. This embodiment may also include one or more of the features listed above in any suitable combination.

Further disclosed herein is a method of cosmetically improving the appearance of a target portion of discolored skin. The method includes identifying a target portion of skin in need of treatment, for example, a discolored portion of skin in the undereye area, and applying a cosmetic composition thereto using the applicator described here. Application of the cosmetic composition to a dyschromic portion of periorbital skin results in a Color Improvement Value of at least about 1% and/or a ΔE of less than about 10. In some instances, the cosmetic composition used in the method has an L* value of from about 30 to 80, a c* value of from about 10 to 50, and an h* value of from about 30 to 80.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

DEFINITIONS

"Active" means a compound that provides an acute and/or chronic benefit to a target biological feature (e.g., system, organ, portion thereof or a type of cell commonly found therein). For example, skin-care actives may regulate and/or improve skin or its associated cells (e.g., improve skin elasticity; improve skin hydration; improve skin condition; and improve cell metabolism).

"Applicator" means a device used to apply a personal care composition to a target surface. A "pre-loaded applicator" is an applicator that includes at least one unit dose of a personal care composition when packaged for sale.

"Cosmetic composition" means a composition that is intended to provide a desired visual effect on an area of the human body. The visual cosmetic effect may be temporary, semi-permanent, or permanent. Some non-limiting examples of "cosmetic products" include products that leave color on the face, such as foundation, mascara, concealers, eye liners, brow colors, eye shadows, blushers, lip sticks, lip balms, face powders, solid emulsion compact, and the like. It is to be appreciated that a cosmetic composition may provide both a cosmetic benefit and a skin health benefit.

"Dermatologically acceptable" means that the compositions or components thereof so described are suitable for use in contact with human keratinous tissue without undue toxicity, incompatibility, instability, allergic response, and the like.

"Disposed" refers to the placement or position of one element relative to another element, where the elements are connected to or in physical contact with one another. For example, when a first element is disposed on a second element, the first and second elements may be joined together or formed together to provide an integral or unitary article. A first element may also be disposed on a second element when the first element is applied to the second element, for example, by a printing method or a coating method.

"Joined" means configurations whereby an element is directly secured to another element by affixing the element directly to the other element, and configurations whereby an element is indirectly secured to another element by affixing the element to intermediate member(s) that in turn are affixed to the other element.

L*a*b* and/or L*C*h* refer to the commonly known color model represented by a three-dimensional 1976 CIELAB color space. L*a*b* is the Cartesian representation whose axes are defined by Lightness, a-value (green to red) and b-value (yellow to blue), and L*C*h* is the cylinder whose axes are defined by the dimensions of Lightness (L*), Chroma (c*) and Hue (h*). Color values are reported at D65/10° lighting/observer or D65/2° lighting/observer unless noted otherwise.

"Natural looking" and variations thereof refer to a cosmetic benefit that does not appear to be provided by a cosmetic composition (i.e., appears as a naturally occurring feature of the face or body). A cosmetic benefit may be deemed to be natural looking by using a conventional visual grading test. For example, a natural looking cosmetic benefit may not be readily noticeable by the human eye at a distance of 75 centimeters under standard lighting conditions. In some instances, a natural looking cosmetic benefit may be characterized by the lack of a "grainy" appearance (i.e., the lack of visually noticeable discrete dots or islets of cosmetic composition on the target surface). Alternatively or additionally, a natural looking cosmetic benefit may be defined as providing a Color Improvement Value of at least a 1% and/or a CIELAB Delta-E 76 ("ΔE") value of less than 10 according to the Color Test, which is described in more detail below.

"Normal skin" is skin that does not include a perceived blemish. "Normal colored skin" is skin that does not include any perceived discoloration and generally matches the color of nearby normal skin. In some instances, it may be desirable to evaluate a perceived blemish such as periorbital dyschromia by comparing the target area of skin comprising the blemish (e.g., undereye area) to nearby normal skin and/or normal colored skin (e.g., on the cheek or forehead) in order to generate a quantitative value that corresponds to a relative difference in skin tone (e.g., Color Improvement Value).

"Periorbital dyschromia" is a condition that occurs when the tone of skin in the periorbital region of a person is noticeably different from the tone of skin in a nearby portion of the face, such as the cheek, nose, forehead, temple and/or another portion of the periorbital region. Perioribital dyschromia is bilateral, (i.e., it occurs in the periorbital region of both sides of the face). Periorbital dyschromia may appear as a result of hyperpigmented and/or hypopigmented skin disposed in the periorbital region.

"Skin care" means regulating and/or improving skin condition. Some nonlimiting examples of skin care benefits include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin texture or smoothness, improving skin exfoliation or desquamation, plumping the skin, improving skin barrier properties, improve skin tone, reducing the appearance of redness or skin blotches, and/or improving the brightness, radiancy, or translucency of skin. Skin care products are products that provide one or more of the foregoing benefits. Some nonlimiting examples of skin care products are described in U.S. Publication Nos. 20080206373 and 20100189669.

"Solid" when referring to the physical state of a cosmetic composition herein means that the composition does not flow at room temperature (i.e., between 20 and 25° C.) under only the effect of gravity when the applicator upon which the composition is disposed is used as intended.

"Substrate" means a material capable of forming a base to which another material or a composition can be applied.

"Transferrable" refers to a composition that preferentially bonds (e.g., adhesively) with a target surface when contacted with the target surface. For example, a transferable composition disposed on a surface of an applicator described herein preferentially bonds to a skin surface when contacted with the skin surface relative to the surface of the applicator upon which the composition is disposed. The transferable composition herein exhibit at least 50% transferability according to the transfer test.

"Undereye area" means the portion of a human face that is located generally near the lower orbital bones (i.e., the maxilla and zygomatic bones) within the periorbital region of the face. In most people, the undereye area extends laterally from the bridge of the nose to the side of the face and is bounded by the eye and cheek.

"Unit dose" means an amount of cosmetic composition transferred to the skin sufficient for a single use of the applicator by the user and that provides a cosmetic effect to the area of application.

At least some consumers desire a cosmetic product that reduces the appearance of perceived skin blemishes, but still provides a natural look (i.e., appears as if there is little or no makeup on the skin). This can be particularly desirable for consumers who use cosmetics to conceal discoloration around the eye, sometimes referred to as "undereye dark circles" or "periorbital dyschromia", as well as other skin blemishes on the face or body, such as age spots. Until now, it was not recognized that an applicator preloaded with a transferable cosmetic composition arranged as a discontinuous pattern of dots can provide a suitable, natural looking cosmetic benefit when the cosmetic composition is transferred to the skin by specifically selecting the color, pattern, and/or opacity of the dots on a substrate.

Cosmetic Applicator

The cosmetic applicator disclosed herein enables a user to conveniently apply a cosmetic composition to a target skin surface and achieve a consistent natural looking cosmetic benefit. The present applicator may be formed as a single layer of material or two or more layers of the same or different materials. For example, the applicator may include a backing layer, a composition layer, and, optionally, a release layer and/or cover layer, each of which is described in more detail below. Each layer may be configured as one or more layers. The backing layer stably supports the composition layer and any optional layers. "Stably support"

means that the physical features of the applicator (e.g., shape, composition and relative positions of the applicator elements) will remain substantially unchanged when subjected to the forces typically encountered prior to and during use of the applicator, such as during routine processing, shipping and handling. The optional release layer may be included to reduce the surface energy of the backing layer and/or improve the transferability of the composition. Of course, it is to be appreciated that any suitable method of reducing the surface energy of the backing layer may be used herein to facilitate transferability of the cosmetic composition. The composition layer may be disposed directly on the backing layer or on the release layer, if included, and includes at least one unit dose of the cosmetic composition. The optional cover layer may be provided to protect the cosmetic composition from contacting non-target surfaces (e.g., clothes) and/or environmental contaminates (e.g., dust) and/or help prevent the loss of volatile ingredients in the composition.

In some instances, it may be desirable to shape the applicator to correspond to the portion of the body to which the cosmetic composition is to be applied (e.g., the undereye region). In this way, a user may be able to more intuitively position the applicator in the intended location by aligning the shape of the applicator with the corresponding body feature. For example, to accommodate the bilateral symmetry of the human face, the cosmetic applicator may be configured to have a right and left version, as desired.

In some instances, it may be desirable to include a tab, handle or other graspable feature, which allows a user to more easily grasp and/or manipulate the applicator without contaminating the cosmetic composition and/or a non-target surface (e.g., clothes, upholstery, or other portions of the body). For example, the applicator may be configured to include a handle that is integral and substantially in the plane of the backing layer. In this example, the user will typically hold the handle between a thumb and forefinger, such that cosmetic applicator lies substantially within the plane formed between these two digits. In some instances, the graspable portion may be formed by attaching a suitable material to a side or a rearward surface of the cosmetic applicator. The graspable portion of the applicator may be configured to be creased, folded and/or flat-packed with the cosmetic applicator.

FIG. 1 shows an example of a cosmetic applicator 10 suitable for use herein. The cosmetic applicator 10 includes a backing layer 20 and a cosmetic composition 30 disposed on the backing layer 20 as a discontinuous pattern of dots. "Discontinuous" means an arrangement generally comprising gaps or breaks in what would otherwise be a continuous configuration. Some non-limiting examples of discontinuous patterns include a multitude of discrete dots, a pattern of lines (e.g., checkerboard or random pattern); a continuous film comprising holes; a film of cosmetic composition disposed on a porous substrate (e.g., fibrous non-woven material) wherein at least some of the pores do not contain the cosmetic composition.

The applicator 20 illustrated in FIG. 1 is substantially crescent-shaped to correspond to the undereye area of a user. The applicator 20 in this example is intended for use with the left undereye region (from the perspective of the user). That is, a user may grasp the applicator 20 at the graspable end 26 such that the broad end 24 of the applicator 20 can be placed near the innermost portion of the undereye area of a user. The graspable end 26 of the applicator 20 is narrower and more elongated than the broad end 24 to facilitate grasping and/or holding of the applicator 20 by a user. As the graspable side 26 is intended to provide a tab or similar grasping means, it may be desirable to include little or even no cosmetic composition on this portion of the applicator 20. The broad end 24 is sized and shaped to correspond to the inner undereye area proximate the nose and, as illustrated in FIG. 1, may include a higher amount of cosmetic composition 30 than the graspable end 26. This may be desirable because, in some instances, the innermost portion of the undereye region (i.e., the portion that is closer to the bridge of the nose) may exhibit more discoloration than other portions of the periorbital region when certain types of periorbital dyschromia are present. While this example illustrates a cosmetic applicator 20 shaped to correspond to the shape of the undereye region, it is to be appreciated that the applicator may be provided in any shape, as desired.

Figure 2:
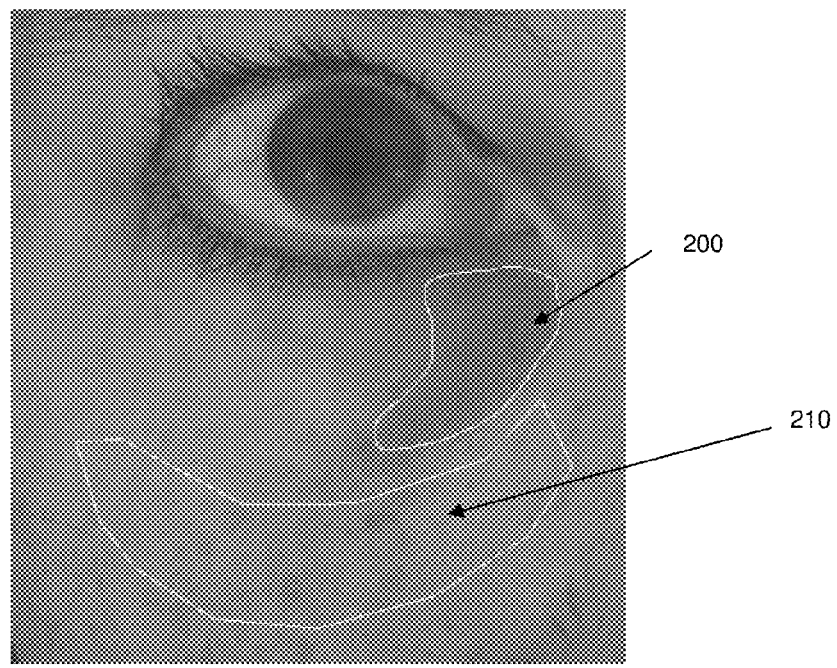
FIG. 2 is an image of a face that includes the periorbital region.

FIG. 2 illustrates a portion of the undereye region 200 of the right eye of a person. The undereye portion 200 shown in FIG. 2 corresponds to the "inner" area of the undereye region and includes periorbital dyschromia. As can be seen in FIG. 2, the undereye portion 200) is noticeably darker than the adjacent non-discolored skin portion 210. Thus, for this example, it may be desirable to distribute the cosmetic composition on the applicator as illustrated in FIG. 1 (i.e., higher density of composition on area of applicator that is intended to be placed near the inner area of the undereye region where the discoloration is most prevalent). However, it is to be appreciated that the cosmetic composition may be distributed in a variety of different ways to correspond to one or more different types of periorbital dyschromia.

In some instances, it may be desirable to configure the present cosmetic applicator to be soft, pliable and/or compressible such that it is comfortable and convenient to use on skin (e.g., in the undereye area), but resilient enough to suitably resist the forces experienced during use and manufacturing. For example, when the present applicator is intended for use in applying a personal care composition to the undereye area, the applicator should be pliable enough to conform to the curvature of the face, but rigid enough to ensure that it does not undesirably bend, fold, wrinkle or collapse when a user attempts to use or position the applicator. This may be especially important if the applicator is being used one-handed.

In some instances, the applicator or a portion thereof (e.g., one or more applicator layers) may be compressible (i.e., the thickness of the applicator or applicator portion can be effectively reduced with the application of a suitable amount of pressure). When applying a composition to a hard-to-reach area of the body such as the undereye area, a user may not apply a consistent amount of pressure to all portions of the applicator. But with a compressible applicator or applicator layer, at least some of the force applied by the user to the applicator may be absorbed and/or more evenly distributed, which may help provide a more consistent and reproducible cosmetic benefit.

The applicator and/or the backing layer (since the backing layer may be the primary or even sole contributor to certain physical characteristics of the applicator) may be formed from a polyethylene film material having one or more of the following properties as determined according to conventional methods known in the art: (i) a density of from 30 to 100 kg/m$^3$; (ii) a thickness of from 0.5 to 6 mm, 1 to 5 mm, 2 to 4 mm or even about 3 mm; (iii) a compression strength of from about 34 kPa to 83 kPa at 25% compression and from about 103 kPa to about 186 kPa at 50% compression; (iv) a tensile strength (i.e., stress) of from about 262 kPa to about 1262 kPa; and (v) a tear resistance of between about 1225 N/m and 6305 N/m. By providing a backing layer with these properties, it is believed, without being limited by theory, that the resulting applicator will have a suitable balance of strength and flexibility for the intended use of delivering a cosmetic composition to a hard to reach portion of the body, such as the periorbital region of the face.

In some instances, transferring less than 50% of the cosmetic composition present on the applicator may result in an inconsistent and/or less natural looking cosmetic benefit, which is contrary to the desired effect of the present applicator. Thus, it is important that at least 50%. 60%, or even at least 70% (e.g., at least 80%, 90%, 95%, and ideally 100%) of the cosmetic composition disposed on the present applicator be transferred from the applicator to the target surface during normal use. To help maximize the amount of composition transferred, it may be desirable to ensure that the applicator is configured (i.e., the individual elements are selected and arranged) to provide a composition that preferentially bonds to skin, relative to the applicator surface upon which the cosmetic composition is disposed. This may be accomplished, for example, by selecting a suitable backing layer material, modifying the physical and/or chemical properties of the backing layer material and/or including a suitable release layer. The transferability of the composition can be determined according to the Transferability Test described in more detail below.

The applicator herein provides a more natural looking cosmetic benefit to a target skin surface than conventional applicators by making a discolored portion of skin appear more like the normal skin nearby. In some instances, it may be important for the discontinuous film of cosmetic composition to have a particular pattern, color and/or opacity to provide the more natural looking cosmetic benefit. Providing a discontinuous film of cosmetic composition on the target skin surface enables the color of the underlying skin to break up the color of the cosmetic composition, which helps create a camouflage effect. It has been particularly discovered that when the discontinuous film of cosmetic composition is in the form of a multitude of dots, the pattern in which the dots are arranged, the opacity of the dots and the area of the applicator covered by the dots can all be important to providing a natural looking cosmetic benefit on a target skin surface. As used herein, the term "dot" means a discrete unit of cosmetic composition that does not touch any adjacent dots when disposed on the applicator and/or the target skin surface.

In some instances, it may be desirable to arrange the dots in a stochastic pattern on the applicator (i.e., a substantially random pattern generated by probabilistic determination), which can then be transferred to a target skin surface. The human eye is capable of readily detecting patterns such as geometric shapes, straight lines (especially at the edges of a pattern), and solid colors and forms, which the brain then tries to process into a recognizable image. When presented with a multitude of dots such as in the present applicator, the brain may connect the dots with an imaginary line as it attempts to discern a pattern or object. But arranging the dots in a stochastic pattern reduces the chance that geometric shapes or straight lines will be perceived by an observer, thereby improving the natural look of the cosmetic benefit. By using a stochastic pattern, the spacing between adjacent dots is substantially non-uniform. For example, a first dot that is adjacent to two other dots (e.g., 3, 4, 5, 6, 7, 8, 9 or 10), will be spaced further from one of the adjacent dots than the other. In this example, the first dot may be spaced away from one adjacent dot by a distance of 50 microns and spaced away from another adjacent dot by 100 microns. Although less preferred, the present applicator also contemplates dots arrangements in the form of certain geometric packing patterns (e.g., hexagonally packed), which can provide a natural look in some instances.

The shape of the dots used in the discontinuous films herein is not particularly limited and may include, for example, curves, lines, curvilinear shapes, rectilinear shapes and combinations of these. Dots that are substantially circular or rounded may be particularly suitable for herein (e.g., for ease of manufacturing, computer modeling, measuring various properties of the composition in situ and the like). In some instances, it may be desirable for the dots to have a radius ratio of less than 20 (e.g., between 1 and 20, between 1 and 15 or even between 1 and 10). It is believed, without being limited by theory, that dots having a radius ratio in this range may provide a more natural looking benefit because the human eye is less likely to perceive edges or geometric shapes in the pattern in dots. The radius ratio of a dot or dot pattern may be determined according to the method described in more detail below.

The cosmetic composition herein may cover from 10 to 50% (e.g., between 15 and 40% or even between 20 and 30%) of the surface area of at least one side of the applicator or, in some instances, a portion of one side, such as the portion corresponding to inner eye area. The area of coverage, which is provides an indication of dot density (i.e., the number of dots per unit area), generally decreases from the inner portion of the applicator near the center to the outer portion of the applicator near the edges. That is, there are generally more dots per unit area near the inner portion of the applicator than at the outer portion. For example, the inner portion of the applicator may have a 50% greater area of coverage than the outer portion (e.g., 10%, 20%, 30%, or 40%). In this example, the inner portion of the applicator may correspond to a portion of the target skin surface in need of the most cosmetic benefit, and the edges of the applicator may correspond to the area of the target skin surface that is nearest normal skin. This effect is sometimes referred to as "feathering." By feathering the cosmetic benefit, the most discolored portion of the target skin surface typically receives the most cosmetic composition and exhibits a relatively large change in color, whereas the more normal-colored portion of the target skin surface typically receives less of the cosmetic composition compared to the more discolored portion and exhibits a relatively small change in color. Thus, the overall color of the target skin surface appears more uniform and closer to the color of the nearby normal skin. The change in color can be determined according to the Color Test below.

Figure 3:
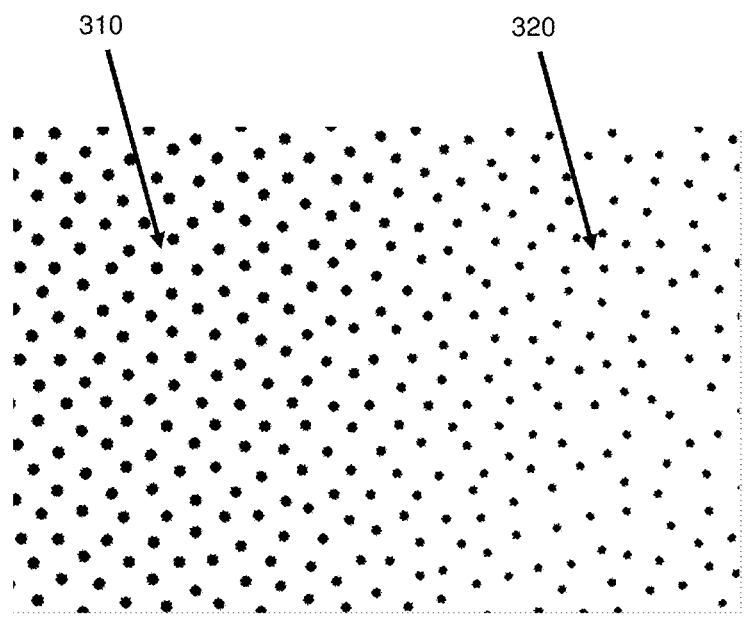
FIG. 3 is an illustration of an exemplary dot pattern.

It is to be appreciated that the applicator herein may be configured such that any portion of the applicator has a greater area of coverage than any other portion, depending on the desired use of the applicator. The change in area of coverage from one portion of the applicator to another portion may occur as a stepwise change or as a substantially regular rate of change (i.e., a gradient). In either case, the change in area of coverage should be sufficiently gradual to minimize the presence of visually detectable artifacts (e.g., lines, shapes, edges). Area of coverage can be determined according to the test method described in more detail below. FIG. 3 illustrates an example of a stochastic pattern of dots where the dot density decreases from a high-density portion 310 to a low-density portion 320. In addition to a change in density, the dot pattern illustrated in FIG. 3 also shows a change in the size of the dots from the high-density portion of the pattern toward the edge. That is, the dots disposed in the higher density portion 310 are larger than the dots disposed in the lower density portion 320.

Figure 4:
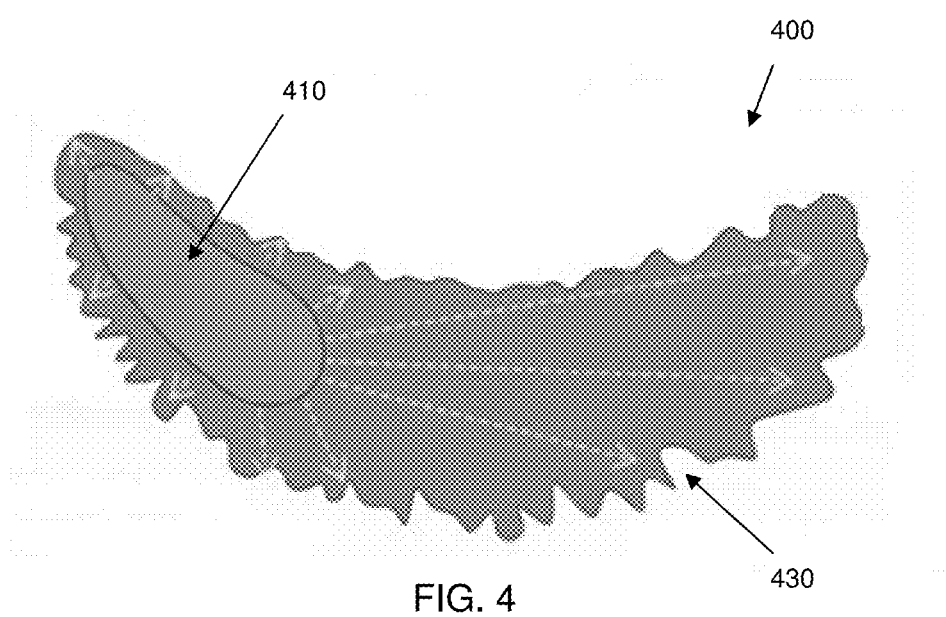
FIG. 4 is an illustration of a plan view of an applicator.

FIG. 4 illustrates an example of an applicator 400 that has a high-density portion of dots 410 in the inner portion of the applicator 400. The dot density decreases outwardly from the high-density portion 410 toward the perimeter 430 as represented by the dashed arrows. When an imaginary line is drawn to connect the dots at the perimeter 430 of the applicator 400, an irregular or serrated edge is defined (referred to herein as a "diffuse" edge). The diffuse edge reduces the chance that a user will perceive any boundaries or other objects that make the cosmetic composition and/or benefit appear less natural looking on the skin.

Figure 5:
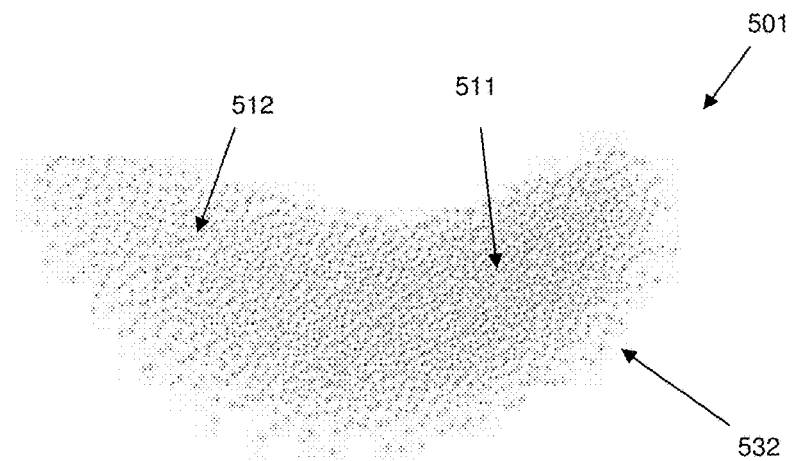
FIG. 5 is an illustration of an exemplary dot pattern.

FIG. 5 illustrates an example of a pattern 501 of a discontinuous pattern of dots as described in FIG. 4. As seen in FIG. 5, a first portion 511 of the pattern 501 has a relatively high Area of Coverage compared to a second portion 512. The dot pattern 501 also provides a diffuse edge 532.

When providing the more natural looking cosmetic benefit herein, the opacity of the dots of composition can be an important factor to control. If the dots are too opaque, then the cosmetic composition becomes more noticeable on the skin and the benefit becomes less natural looking. On the other hand, if the opacity of the dots is too low, then the cosmetic composition may not deliver the desired amount of cosmetic benefit (e.g., may not provide sufficient coverage to suitably reduce the appearance of the target skin blemish). Dot opacity is primarily a function of dot size and pigment loading in the cosmetic composition. Color Contrast is used herein to characterize the opacity of the dots. A Color Contrast Value can be determined according to the method described in more detail below. Dots suitable for use with the present applicator may have a Color Contrast Value of between 0.1 and 0.9, for example, from 0.1 to 0.6 or even from 0.2 to 0.5, when measured according to the Opacity Test.

Figure 6:
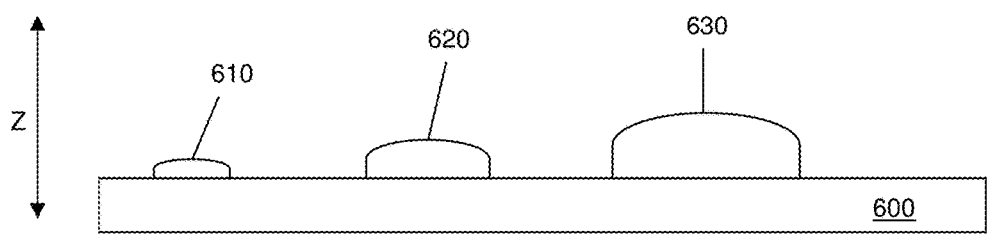
FIG. 6 is an illustration of different sizes of dots.

FIG. 6 illustrates how the change in dot size can alter the opacity of the dot. As illustrated in FIG. 6, three different sized dots 610, 620 and 630 are disposed on a substrate 600. The size of a dot is typically increased by applying more cosmetic composition to the substrate 600. When a relatively small amount of composition is applied, a relatively small dot 610 is formed. However, when more cosmetic composition is applied, the dot size increases as demonstrated by dots 620 and 630. Since the size of the dot will typically increase in all three dimensions, including the Z-dimension (i.e., thickness) as represented by the arrow in FIG. 6, the amount of light that can pass through the dot will be reduced, thereby increasing the opacity of the dot. Thus, when formed from the same cosmetic composition, the smallest dot 610 will have the lowest opacity, followed by the medium dot 620. And the largest dot 630 will have the highest opacity.

Dot sizes suitable for use with the applicator herein include dots having a maximum dimension of between 10 μm and 300 μm (e.g., between 10 μm and 250 μm; 40 μm and 200 μm; 50 and 150 μm; or even between 75 μm and 100 μm). Dot size can be determined according to the Dot Size Test described in more detail below. It is to be appreciated that the process used to place the dots of cosmetic composition on the target substrate (e.g., backing layer) may create dots that are not all shaped the same and/or that include irregular shapes. Consequently, it may be desirable to characterize the dots using a Radius Ratio. The Radius Ratio of a dot herein may be less than 20 and greater than or equal to one (e.g., 1, 2, 3, 4, 5, 6, 7, 8, 9, 10, 11, 12 or 13 when rounded to the nearest integer according to generally recognized rounding practices) and can be determined according to method described in more detail below.

While certain examples herein may describe applicators having only one size of dots disposed thereon, it is to be appreciated that present applicator may include dots of two or more sizes (e.g., 2, 3, 4, 4, 6, 7, 8, 9, 10) that are arranged in any suitable pattern desired. For example, an applicator may include 3 different sizes of dots that are interspersed throughout a stochastic pattern.

The color of the cosmetic composition is an important factor in providing a natural looking cosmetic benefit. The color of the cosmetic composition should be selected to provide a suitable color match to the normal skin color of the user. In some instances, suitable ranges of color for the cosmetic composition herein include $L^*C^*h^*$ D65/10° values of: $L^*$ from 30 to 80 (e.g., from 50 to 75 or even from 55 to 70); $C^*$ from 10 to 50 (e.g., from 20 to 40 or even from 20 to 35); and $h^*$ from 30 to 80 (e.g., from 45 to 75 or even from 50 to 65). It is believed, without being limited by theory, that the foregoing ranges can provide a suitable color match to those individuals characterized as having a Fitzpatrick skin type of I, II, III or IV according to the Fitzpatrick Scale, which is well known in the field of cosmetics. It is further believed, that by knowing the foregoing $L^*C^*h^*$ values, the skilled artisan could readily provide a suitable color match for individuals having a Fitzpatrick skin type of V or VI. The color of the composition can be determined according to the Composition Color Test described below.

When used as intended, the applicator herein can provide a natural looking cosmetic benefit defined by a $\Delta E$ value of less than 10 (e.g., less than 6 or less than 3 and ideally 0), relative to normal skin and/or a Color Improvement value of at least 1% up to, ideally, 100% (e.g., any value between 1% and 100%). The $\Delta E$ value can be determined according to the Color Test, and the Color Improvement value can be determined according to the Color Improvement Test, each being described below. It is important to provide a suitable $\Delta E$ so that the cosmetic composition matches the color of normal colored skin, thereby reducing the likelihood that the applied cosmetic composition will be noticed by an observer. It is also important for the cosmetic composition, when applied to a perceived skin blemish such as periorbital dyschromia, to provide a suitable Color Improvement value to better camouflage the blemish such that is appears more like normal colored skin.

The cosmetic applicator herein may be made using any suitable conventional manufacturing process. For example, the applicator may be made using a conventional assembly line-type process where a continuous supply of backing layer material (e.g., fed from a roll of material) is placed on a conveyor belt or similar transport means and the cosmetic composition and/or other optional layers are placed on the backing layer material at various stages of the process. Additionally or alternatively, the applicator may be made using a batch process where discrete sheets of backing layer material are provided and the cosmetic composition and/or any optional layers are attached to the sheet. The optional release layer is typically placed on the backing layer prior to the cosmetic composition and may be placed on the backing layer material by any suitable means known in the art (e.g., a coating and curing process). The cosmetic composition may be placed on the backing layer material and/or release layer in one or more layers via a printing process such as screen printing, gravure roll printing, flexographic printing, ink jet printing, and the like and combinations of these. A particularly suitable printing process is gravure roll printing, which has been found to provide a suitable balance between cost, ease of manufacturing, and dot size and fidelity. The cosmetic composition may be provided as a single layer comprising a colorant dispersed in an adhesive matrix or other suitable carrier. In some instances, the cosmetic composition may be applied to the backing layer substrate as one or more layers of the same or different colorant-containing composition(s) followed by the application of one or more layers of the same or different adhesive-containing composition(s), which are applied, for example, via a registration printing process (i.e., a printing process wherein the adhesive-containing composition(s) is precisely placed on top of the colorant-containing composition(s)).

The applicator may be formed to the desired size and shape using a suitable cutting means such as a conventional die cutting process. The applicator may be sized and shaped at any step during the manufacturing process. For example, the backing layer may be shaped and/or sized before and/or after application of cosmetic composition. In another example, the applicator may be sized and/or shaped after application of the cosmetic composition and optional release layer, but before the placement of an optional cover layer. In this example, one or more cosmetic-containing applicators may be placed on a rigid support structure (e.g., cardboard or card material) to provide a suitable package for commercial sale. Continuing with this example, the optional cover layer may be placed over the applicator(s) after being joined to the rigid support structure such that a sealed package is provided. The cover layer may be configured to be reclosable so as to enable convenient removal of an applicator but still provide a suitable barrier over any remaining applicators in the pack when the cover layer is replaced. In still another example, a cover layer may be placed over a cosmetic-containing applicator that has been joined to a rigid support material. In this example, the applicator may then be cut to the desired size and/or shape (e.g., via die cutting), thereby providing individual applicators suitable for commercial sale. The individual applicators can then be packaged together loosely in packages of two or more applicators or sold individually.

Backing Layer

The backing layer, cosmetic composition layer, optional release layer and optional cover layer may be formed from any suitable material known for making such layers, as long as it provides the desired properties to the applicator. For example, the backing layer may be formed from foam materials (open and/or closed cell); films; fibrous materials such as woven and/or non-woven materials made with natural and/or synthetic fibers; cellulosic materials such as paper; and combinations of these. In some instances, it may be desirable to provide a backing layer that includes a foam material that is pliable and compressible, but still provides a suitable amount of physical resilience. A particularly suitable example of a material for use in the present applicator (e.g., as the backing layer) is VOLARA Type A brand foam available from Sekisui Voltek, LLC.

Release Layer

In some instances, it may be desirable to include an optional release layer in the present applicator which provides a suitable boundary layer between the cosmetic composition and the backing layer. The release layer should be capable of forming a bond with the cosmetic composition (e.g., adhesive, cohesive, electrostatic) that is strong enough to retain the cosmetic composition on the applicator during non-use conditions (e.g., manufacturing, shipping and handling) but weak enough to enable the composition to be transferred to a target skin surface under normal use conditions (e.g., the application of a pressure of greater than 50 g/cm$^2$). The release layer may be coated directly on the backing layer, for example, as a liquid composition and/or the release layer may be a solid substrate joined to the backing layer by a suitable bonding means.

The release layer may be configured to help prevent the personal care composition from penetrating into the backing layer and/or to alter other characteristics of the backing layer (e.g., coefficient of friction, surface energy, chemical properties). For example, the release layer may occlude the pores of a porous backing layer substrate to reduce the mechanical bonding forces between the backing layer and the personal care composition, which improves the transferability of the personal care composition to a target skin surface. The release layer may also provide a relatively flat surface on which to deposit the personal care composition, which reduces the variation in height or angle of the dots of cosmetic composition and thereby improves how evenly the composition can be transferred to the target skin surface.

The release layer material may be included to provide a lower surface energy surface relative to the backing layer. For example, the release layer may have a surface energy of from 18 dyne/cm to 30 dyne/cm. The release layer may be formed from any suitable material known in the art. A particularly suitable example of a release layer is a radiation curable silicone such as TEGO brand silicones available from Evonik Industries AG, Germany, which can be applied to the backing layer at between 0.5 and 2.0 g/m$^2$ by any suitable means known in the art (e.g., roller coating) and then cured. Additionally or alternatively, the release layer may include a powder coating layer. For example, the powder coating layer may be applied before, during and/or after the silicone layer is applied and/or cured. The powder may be configured such that at least some of the powder is transferred along with the personal care composition during use. The powder may provide an aesthetic benefit such as a matte look and/or reduce the perceived tackiness of the personal composition after it is applied to the target skin area.

Cosmetic Composition Layer

The present applicator includes a layer of cosmetic composition disposed on the backing layer and/or release layer of the applicator. The cosmetic composition herein includes an adhesive material, one or more colorants and, optionally, one or more additional ingredients such as actives, carriers, emulsifiers, and thickeners. Some nonlimiting examples of optional ingredients that may be included in the present cosmetic composition are disclosed in U.S. Publication No. 2008/0206373 and in the CTFA Cosmetic Ingredient Handbook, Second Edition (1992).

It can be important to provide a suitable amount and/or type of colorant and/or other ingredients in the cosmetic composition that affect the opacity of the cosmetic composition. The colorants suitable for use herein are not particularly limited, as long as they provide the desired natural looking cosmetic benefit. In some instances, the colorants are pigment particles selected to provide the particular range of color values (i.e., L*c*h* values). The pigment loading level should be high enough to provide the desired cosmetic benefit (e.g., coverage of a perceived skin blemish), but low enough to provide the desired opacity, color and/or rheology of the cosmetic composition. Pigment may be included in the cosmetic compositions at from 0.1% to 50% by weight of the liquid composition.

The colorant may include any suitable pigment, dye or lake approved by the U.S. Food and Drug Administration for topical use on skin. Some non-limiting examples of pigments include cosmetic grade talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, bismuth oxychloride, combinations thereof and the like. Pigments that are generally recognized as safe are listed in C.T.F.A. Cosmetic Ingredient Handbook, 3rd Ed., Cosmetic and Fragrance Assn., Inc., Washington D.C. (1982). The cosmetic composition may include a single colorant to provide the desired color, or two or more colorants may be used in combination.

The adhesive material may include any suitable adhesive known for topical use on skin. Suitable examples of adhesive include pressure sensitive adhesives selected, for example, from acrylic polymers (e.g., acrylate and methacrylate copolymers), and rubber-based or styrene copolymer-based pressure sensitive adhesives such as styrene-isoprene-styrene (SIS), or styrene-butadiene-styrene (SBS) copolymers. Some non-limiting examples of pressure sensitive adhesives, which can be used alone or mixed with other pressure sensitive adhesives, include water based adhesives commonly used for temporary tattoos (e.g., SP310 available from Chromaline, GFGN-6924 available from Colorcon and Craigbond 3256Z (sold as FGN-6924 by Colorcon). In some instances, the adhesive may be present at an amount of at least 50%, but typically less than 100% (e.g., from 55%-90%; 60%-80%; or even 65%-75%). In some instances, the ratio of pigment to adhesive may be from 1:10 to 1:1 in the dry composition.

The adhesive material and colorant may be mixed together using conventional processing techniques such that the colorant is dispersed throughout a matrix of the adhesive material. In some instances, the adhesive material and colorant may be applied to the applicator as separate compositions.

Cover Layer

The present applicator may include a protective cover layer removably attached to the personal care composition and/or one or more other layers of the applicator. The protective cover layer is provided to prevent undesirable contact with and/or contamination of the personal care composition and is intended to be removed just prior to use. The cover layer may be water or vapor impermeable to help minimize the loss of any liquid or volatile components from the personal care composition. The cover layer may be configured to cover only the portion of the applicator that contains the personal care composition, or it may extend beyond the composition containing portion of the applicator, as desired. The cover layer may be a thin film (e.g., having a thickness of about 85 microns, from 85 microns to 130 microns, or even from 90 microns to 120 microns). The protective layer or portions thereof may be transparent, semi-transparent, translucent or opaque. For example, the cover layer may include one or more transparent, semi-transparent, translucent and/or opaque portions. The cover layer may include indicia that correspond to a cosmetic benefit or pattern provided by the applicator. In some embodiments, the cover layer may include instructions and/or illustrations relating to at least one aspect of the usage of the applicator. The protective cover layer may be formed from any suitable material known in the art. In some instances, the cover layer may include a coating of a non-stick material such as a suitable wax, silicone, fluorosilicones or fluoropolymer (e.g., TEFLON brand polytetra-flouroethylene available from DuPont).

Figure 7:
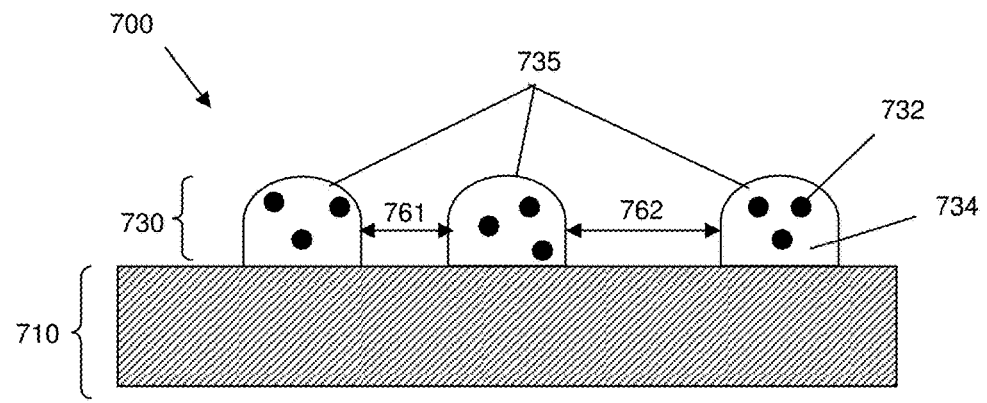
FIG. 7 is a side view of an example of an applicator

FIG. 7 illustrates an example of the present applicator 700 that includes a backing layer 710 with a cosmetic composition layer 730 disposed thereon. The cosmetic composition layer 730 is configured as a discontinuous layer of discrete dots 735. The dots of cosmetic composition 735 include a colorant in the form of pigment particles 732 dispersed in a matrix of adhesive 734, which advantageously eliminates the need for a two-step cosmetic application process. The spacing between adjacent dots of cosmetic composition 735, as illustrated by arrows 761 and 762, varies randomly as a result of being configured in a stochastic pattern.

Figure 8:
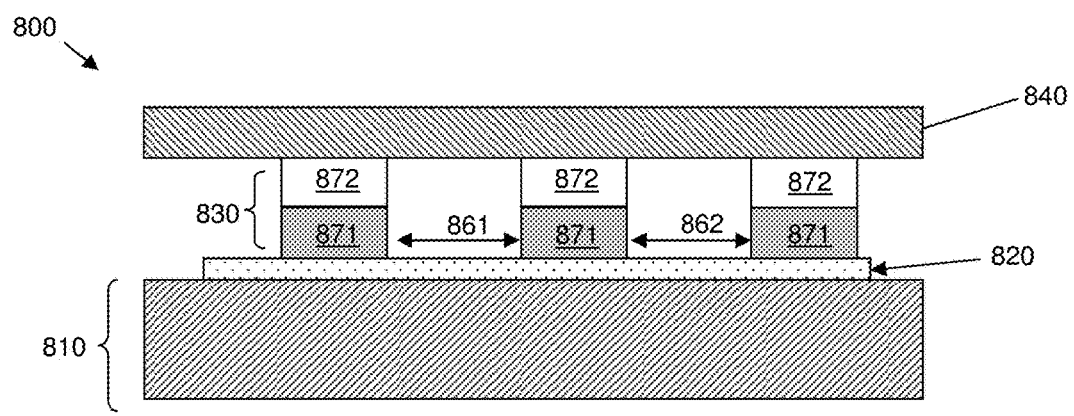
FIG. 8 is a side view of an example of an applicator

FIG. 8 illustrates an example of an applicator 800 that includes a backing layer 810, a release layer 820 configured as a continuous film, and a cosmetic composition layer 830 configured as multi-layer, discontinuous film. In this example, the cosmetic composition layer 830 includes a discontinuous film of colorant 871 and a discontinuous film of adhesive 872 disposed on top of the colorant film 871. In some instances, it may be desirable to include one or more actives in the adhesive film 872. In addition, a cover layer 840 is disposed over the cosmetic composition layer 830. The spacing between adjacent dots 835, as illustrated by arrows 861 and 862, is substantially the same as a result of being configured in a hexagonally-packed pattern.

Figure 9:
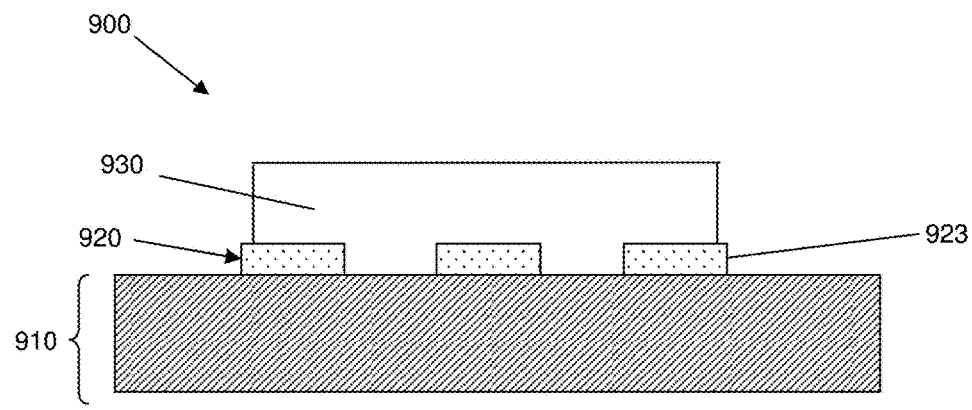
FIG. 9 is a side view of an example of an applicator

FIG. 9 illustrates an example of an applicator 900 that includes a backing layer 910 with a discontinuous release layer 920 disposed thereon and a cosmetic composition 930 disposed on the release layer 920. In this example, the cosmetic composition is provided as a continuous film, while the release layer comprises discrete dots of release material 923. As can be seen in FIG. 9, the cosmetic composition layer 930 may be disposed on top of the release layer 920 as well as between the dots of release material 923, which allows the cosmetic composition to bond with the backing material. The bond formed between the cosmetic composition layer 930 and the backing material layer 910 is stronger than the bond between the cosmetic composition layer 930 and the release layer 920. The bond formed between the cosmetic composition layer 930 and the backing material layer 910 is also stronger than the bond formed between cosmetic composition layer 930 and the target skin surface. Thus, when the cosmetic composition 930 is contacted with the target skin surface, only those portions of cosmetic composition disposed on the release layer will be transferred to the target skin surface, thereby resulting in a discontinuous film of dots of composition on the target skin surface, which provides a more natural looking cosmetic benefit.

Figure 10:
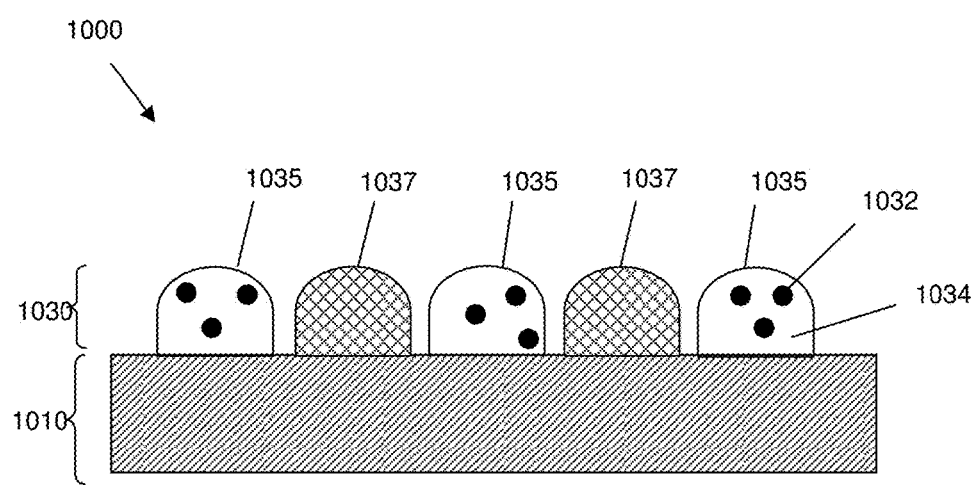
FIG. 10 is a side view of an example of an applicator

FIG. 10 illustrates an example of an applicator 1000 that includes a backing layer 1010 and a cosmetic composition layer 1030. In this example, the cosmetic composition layer includes dots of a pigment-containing cosmetic composition 1035 and dots of an active-containing cosmetic composition 1037. The pigment-containing composition 1035 may include colorant particles 1032 dispersed in an adhesive matrix 1034. The pigment-containing cosmetic composition 1035 and/or active containing composition 1037 may be configured as a discontinuous layer of dots in any suitable pattern (e.g., stochastic), as desired.

Kits

The applicator herein may be sold as part of a kit for cosmetic use. The kit includes at least one applicator and at least one additional cosmetic product selected from one or more additional applicators; skin care products; color cosmetic products such as mascaras, lipsticks and foundations; hair care products such as shampoos and conditioners; and personal care products such as cleansers, deodorants and body washes. The additional product may be selected to be used in conjunction with the applicator as part of a beauty regimen (e.g., a daily grooming routine) and/or the additional product may be used as a standalone product. For example, the kit may include a first applicator configured for use on a first body portion (e.g., the undereye area) and one or more additional applicators for use on one or more different body portions (e.g., other portions of the face, the neck, back, arms, hands, and/or chest). In some instances, the kit may include substantially the same applicator (i.e., same size and shape) but with different types and/or amounts of cosmetic composition. In another example, the kit may include several of the same applicator, which can be used in succession to provide, for example, a buildable cosmetic benefit. In still another example, the kit may include different applicators to treat different conditions or disorders, such as different types of periorbital dyschromia. The applicator and additional product may be packaged together or separately. In some instances, the applicator and additional product may be packaged in separate packages, which are then packaged together in a single package.

In some instances, the kit may include applicators that have different amounts of cosmetic composition disposed thereon. For example, the kit may include a first applicator that has a relatively high amount of cosmetic composition and a second applicator that has a lower amount of cosmetic composition. In this way, a user can customize the cosmetic benefit she desires, for example, by using the applicator with the high amount of cosmetic composition to provide a higher level of concealment. Further, the kit may include applicators that have different regions of coverage. For example, a first applicator in the kit may include a cosmetic composition disposed on the applicator such that the composition will be delivered primarily to the inner undereye region when used as intended. In this example, the kit may include a second applicator that has the cosmetic composition disposed thereon such that the composition is delivered to a larger portion (or even all) of the under region of the user when the applicator is used as intended.

In some instances, the kit may include two or more applicators, package together or separately, but generally located in the same area of a retail environment (e.g., within 3 meters of one another on a store shelf), wherein a first applicator includes a cosmetic composition with a first color profile (e.g., LCh values according to the method herein) and a second applicator with a second color profile that is different from the first. In this way, a user can customize the cosmetic benefit to adjust for normal variations in skin tone (e.g., seasonal changes due to tanning).

Array of Products

The applicators herein may be packaged and sold as an array of products. In some instances, the array may include a first package that includes an applicator for use with a first condition, disorder and/or skin type, and a second package that includes an applicator for use with a second condition, disorder or skin type. The first and second packages include indicia that communicate to a consumer the particular condition, disorder and/or skin type for which the cosmetic composition of each applicator is suited. The array also includes indicia that communicate to a consumer that each package in the array is part of a single product offering, for example, by including the same or similar advertising, package markings, product brand and/or source identifier (e.g., artwork, trademark and/or trade dress). In one non-limiting example, the array may include a first package intended for use by consumers that exhibit a first Fitzpatrick skin type and a second package intended for use by consumers that exhibit a second Fitzpatrick skin type. It may be desirable to position the packages of the array in close proximity to one another in a retail environment, but other embodiments wherein the packages are spaced away from one another are also contemplated. In some instances, different packages of the array may be packaged together as a bundle of packages.

Test Methods

The test methods below provide suitable means for determining certain properties of the present applicator and/or cosmetic composition. Unless otherwise indicated all tests are performed at 23±2° C. and 101±2 kPa.

Color Test

The Color Test uses a spectrophotometer or color calibrated camera (e.g., a modified VISIA system) to measure the color of a target skin surface in L*a*b* color space. This method provide a suitable means for determining the amount of color change needed by and/or obtained from a cosmetic composition applied to a target skin surface. CIELAB Delta-E ("ΔE") 76 is used to describe the difference between colors (i.e., how far apart they are in the L*a*b* color space), and the color values are reported at D65/2°. This method can be used to measure the color difference between two target skin surfaces (e.g., a blemished skin surface and a normal skin surface) or the color change of a target skin surface before and after treatment with a cosmetic composition.

The Color Test can be used to determine the Color Improvement Value of a blemished skin surface (e.g., periorbital dyschromia in the undereye region) that has been treated with a cosmetic composition. To do this, the color of the blemished skin surface (before and after treatment) is compared to normal colored skin (e.g., the cheek).

To determine the Color Improvement Value of blemished skin that has been treated with a cosmetic composition, first measure the L*a*b* values of the blemished skin and normal colored skin, ensuring that the target skin surfaces are clean and substantially free of any contaminants (e.g., make up or dirt). The instrument used to measure the L*a*b* values should have sufficient resolution to measure the blemished portion of skin only. The color difference between the blemished and normal colored skin is calculated as set forth in equation (a) below:

$$\Delta E(\text{Color of blemish vs. color of normal colored skin}) = [(L_{blemish} - L_{normal\ colored\ skin})^2 + (a_{blemish} - a_{normal\ colored\ skin})^2 + (b_{blemish} - b_{normal\ colored\ skin})^2]^{0.5}. \quad (a)$$

Next, apply the cosmetic composition to the blemished skin using the applicator as intended. Measure the L*a*b* values of the treated blemished skin and untreated normal colored skin. The color difference between the treated blemished and the normal colored skin is calculated according to the following equation (b):

$$\Delta E(\text{Color after treatment of blemish vs. Color of normal colored skin after treatment}) = [(L_{blemish\ after\ treatment} - L_{normal\ colored\ skin\ after\ treatment})^2 + (a_{blemish\ after\ treatment} - a_{normal\ colored\ skin\ ater\ treatment})^2 + (b_{blemish\ after\ treatment} - b_{normal\ colored\ skin\ after\ treatment})^2]^{0.5} \quad (b)$$

The Color Improvement Value is calculated by comparing the results from equation (b) to the result from equation (a) according to the following equation (c):

$$\text{Color Improvement Value} = \{1 - \Delta E(\text{Color after treatment of blemish vs. Color of normal colored skin}) / \Delta E(\text{Color of blemish vs. color of normal colored skin})\} \times 100\% \quad (c)$$

100% improvement indicates the treated blemished skin is equal in color to the nearby (treated or untreated) normal colored skin.

The Color Test can also be used to determine the amount of color change created by application of a cosmetic composition to normal colored skin. In order to provide a more natural looking cosmetic benefit, the cosmetic composition should have as little change to the nearby skin color as possible. Hence, a low ΔE value is desirable when the compositions herein are applied to normal skin. Images of a target portion of normal colored skin are taken before and after applying the cosmetic composition to the target skin portion. The L*a*b* values of the normal colored skin are measured from the images before and after application of the cosmetic composition. The ΔE is calculated according to the following equation (d):

$$\Delta E = [(L_{normal\ colored\ skin\ after\ treatment} - L_{normal\ colored\ skin\ before\ treatment})^2 + (a_{normal\ colored\ skin\ after\ treatment} - a_{normal\ colored\ skin\ before\ treatment})^2 + (b_{normal\ colored\ skin\ after\ treatment} - b_{normal\ colored\ skin\ before\ treatment})^2]^{0.5}. \quad (d)$$

Composition Color Test

This method provides a suitable means for determining the color of a cosmetic composition in L*C*h* color space.
1. Using an automatic film applicator such as a Bird Bar, create a uniform, wet film of cosmetic composition over black & white regions of a Leneta card (Opacity Chart 2A). Ensure the film is sufficiently thick such that the color of the underlying Leneta card does not influence the measured L*c*h* values. If the film is sufficiently thick, the measured L*C*h* values over the black portion of Leneta card will be substantially the same as the values measured over white portion.
2. Allow film to dry for 24 hours at room temp and visually ensure film is uniformly dried (even appearance) before measuring.
3. Measure the reflectance of the film over black portion of the Leneta card at 400-700 nm in 10 nm increments using microflash (reflectance spectrophotometer w/ integrating sphere). Record the L*C*h* values at D65/10. Repeat for the white portion of the Leneta card.

Contrast Ratio Test

The Contrast Ratio Test provides a suitable method for determining the opacity of a composition such as dots of cosmetic composition herein. The method below is described using the present applicator, but it is to be appreciated that the method can be readily adapted for use with a composition that is not disposed on an applicator. Further, while method refers to a HIROX brand KH-1300 digital microscope, it is to be appreciated that the method can be adapted for use with any suitable digital image capture device.

Calibration
1. Before beginning the test, it is important to calibrate the digital image captured by the camera to generate a contrast ratio value that is not instrument specific. Calibration may be done according to any suitable calibration method known in the art. For example, the image may be calibrated with a known standard grayscale chart (e.g., a KODAK brand Gray Scale Q-13 calibration chart). This step includes a linear regression to correlate the captured image to the known standard (i.e., gray scale chart), which is well known to those skilled in the art.

Sample Preparation and Image Acquisition

After calibrating the image capture device, place an applicator containing the cosmetic composition on the black portion of a LENETA brand Form 2A opacity chart such that the cosmetic composition contacts the card. Apply 518 g/cm² of pressure for 10 seconds to transfer the cosmetic composition to the card. Carefully peel the applicator off the opacity chart and discard the applicator. Repeat for the white surface of the opacity chart using a new applicator. Capture images of dots from the portion of the sample having the highest density of dots. In order to compensate for dot-to-dot variability, at least 600 dots should be analyzed. Depending on the quality (i.e., resolution) of the camera used to capture the images, several images (e.g., 10 or more) may be required to provide the requisite number of dots. In addition, the total area of each dot in the image should be at least 2500 pixels. One example of a suitable image capture device is an MX-250Z lens in combination with a HIROX brand KH-1300 digital microscope, which can be used for dot sizes in the range of 50-100 um.

Image analysis
1. Process the image from each of the black and white portions of the opacity chart by using suitable imaging analysis software such as Image Pro Premier or equivalent. Suitable image analysis software will allow for the isolation or thresholding of each individual dot from the remainder of the image (e.g., Smart Segmentation Algorithm in Image Pro Premier). Following thresholding, the software will then analyze and output each individual dot's luminous characteristic (i.e., calibrated Y channel intensity).
2. Average the calibrated Y values of all measured dots on the black portion of the opacity chart. Also average the calibrated Y value from all measured dots on the white portion of the opacity chart.
3. Dot opacity is the ratio of the average Y value of all measured dots over black divided by the average & average & value of all measured dots over white.

Dot Size (maximum dimension), Radius Ratio and Area of Coverage Tests—
1. Capture image as in the Contrast Ratio method above.
2. Process the image from each of the black portions of the opacity chart by using suitable imaging analysis software such as Image Pro Premier or equivalent. Suitable image analysis software will allow for the "isolation" or thresholding of each individual dot from the remainder of the image (e.g. Smart Segmentation Algorithm in Image Pro Premier). Following thresholding, the software will then analyze and output each individual dot's spatial characteristics (i.e. dot diameter, area, and radii).
3. Dot size (maximum dimension) is derived by averaging of the maximum diameter of all measured dots on the black portion of the opacity chart.
4. Radius ratio is derived by averaging the radius ratio (ratio between maximum and minimum radius) of all measured dots on the black portion of the opacity chart.
5. Area coverage is derived taking the ratio of total dot area to total area analyzed. If more than 1 image capture is needed, this ratio is determined for each capture and then each of these are average.

Transferability Test

This test method provides a suitable means to determine the amount of composition that transfers from an applicator to a target surface.

Sample Collection
1. Obtain two 4 cm² pieces of black coated Leneta card (e.g., cut 2 cm×2 cm squares out of a standard form).
2. Place the applicator on a hard level surface with the composition-containing side face up.

3. Place the first piece of Leneta onto the applicator (black side applied to composition)
4. Using an appropriate weight, evenly apply 140 g/cm² of pressure (±20 g/cm²) for 10 seconds.
5. Remove the weight and Leneta card from the applicator.
6. Place the second Leneta card onto the applicator in the same way as above.
7. Apply excess pressure to transfer any remaining composition onto the second Leneta square. The second Leneta card should contains all "residual" composition not transferred to the first Leneta card.
8. Visually confirm that all the composition has transferred from the applicator to the second Leneta card.

Dot Area Analysis and % Transfer Calculation
1. Use a microscope with camera (or similar device) to capture images of the composition on the first and second Leneta cards.
2. Calculate the total area occupied by the composition on each Leneta card using suitable image analysis software.
3. Calculate % transfer (onto first Leneta card) as follows:

% Transfer=[(AREA covered by composition on first Leneta card)/(TOTAL AREA covered by composition on both Leneta cards)]*100EXAMPLES Examples 1, 2 and 3 are applicators according to the present disclosure. The applicators in each example include a treated foam backing material and a cosmetic composition printed thereon as a discontinuous pattern of dots. The dots in Examples 1 and 3 are in a stochastic (random) pattern, whereas the dots in Example 2 are in a hexagonally packed pattern. The foam backing material is treated with a silicone release layer to facilitate transfer of the cosmetic composition from the applicator to a target skin surface. The cosmetic composition is made by mixing a pressure sensitive adhesive (PSA) with a pigment to form a slurry. In the case of Example 2, additional water was added to the slurry. The liquid cosmetic composition is printed onto the treated side of the backing material using a gravure printing process. After printing, the applicator is passed through a dryer to remove any excess water from the cosmetic composition. A cover layer is then applied to the dry applicator. Table 1 shows the ingredients used to make the three exemplary applicators.

|  | Ex. 1 | Ex. 2 | Ex. 3 |
|---|---|---|---|
| Backing Layer (thickness) | Crosslinked LDPE, (2 mm) | Closed cell PE-EVA copolymer² (1.15 mm) | Plastic coated PE-EVA copolymer³ (0.95 mm) |
| Release coating (amount used) | Silicone acrylate (1.2 g/m) | Silicone acrylate (1.4 g/m²) | Silicone acrylate (0.95 g/m²) |
| Cosmetic Composition | 60% PSA, 40% Pigment slurry¹¹ | 60% PSA, 20% Pigment slurry¹¹, 20% water | 70% PSA, 30% Pigment slurry¹¹ |

-continued

|  | Ex. 1 | Ex. 2 | Ex. 3 |
|---|---|---|---|
| Cover layer | Kraft Paper⁹ | SBOPP¹⁰ | Kraft Paper⁹ |
| Dot pattern | Random | Hexagonal | Random |

¹Volara Type A available from Sekisui Voltek, LLC
²Volara Type EO available from Sekisui Voltek, LLC
³Volextra Type EVA 1075 GY/GY available from Sekisui Voltek, LLC
⁴TEGO RC902:RC711:A18 (70:30:2) available from Evonik
⁵TEGO RC902:RC711:A18 (70:30:2) available from Evonik
⁶TEGO RC 902:RC922:RC711:A18 (50:20:30:2) available from Evonik
⁷FGN-6924 (Craigbond 3256Z) (emulsion), available from Colorcon, Inc.
⁸SP310 Acrylic copolymer (emulsion), available from Chromaline
⁹44# PK Kraft paper, polypropylene coated on one side, with silicone coating over polypropylene layer, available from Sil Tech (a division of Technicote)
¹⁰Scotchpak 9714 SBOPP, available from 3M
¹¹Pigment Slurry: 60% pigment (79.8% TiO2, 14.62% yellow Fe₂O₃, 5.00% red Fe₂O₃ and 0.58% black Fe₂O₃ by weight, based on the total weight of pigment), 2% Darvan 821A and 38% water Examples 4-6

The applicator from Example 1 above was tested on test subjects to determine the effect of dot size and area of coverage on the benefit provided by the applicator. The number of dots was fixed, and thus the dot size was increased in order to increase area of coverage. Example 4 had an area of coverage of 13.6%, Example 5 had an area of coverage of 22% and Example 6 had an area of coverage of 33.8%. Example 6 had the largest average dot size (i.e., max dimension), followed by Example 5 and Example 4. The results are shown in Table 2 below.

TABLE 2

|  | Example 4 | Example 5 | Example 6 |
|---|---|---|---|
| % Area Covered | 13.6 | 22.0 | 33.8 |
| Contrast Ratio | 0.28 | 0.30 | 0.41 |
| Avg. max dimension | 73.39 | 84.22 | 143.09 |
| radius ratio | 2.22 | 3.44 | 7.18 |
| L, c, h | 62.9; 32.7; 60.6 | 62.9; 32.7; 60.6 | 62.9; 32.7; 60.6 |
| Avg. % color improvement | 1.42 | 5.79 | 7.35 |
| ΔE value | 1.55 | 2.20 | 1.97 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic applicator for providing a natural looking cosmetic benefit, comprising:
    a. a substrate; and
    b. a solid, transferable cosmetic composition disposed on the substrate as a multitude of dots arranged in a discontinuous stochastic pattern, wherein the cosmetic composition comprises a colorant and an adhesive and the composition has an L* value of from about 30 to 80, a c* value of from about 10 to 50, and an h* value of from about 30 to 80,
    wherein the dots have a maximum dimension of between about 10 µm and 250 µm and a radius ratio of between 1 and 10,
    wherein the pattern of dots comprises a diffuse edge,
    wherein the substrate includes a release layer and the cosmetic composition is disposed on the release layer,
    wherein the colorant is a plurality of pigment particles dispersed in the adhesive, and
    wherein a ratio of pigment to adhesive in the composition is from about 1:10 to 1:1.

2. The cosmetic applicator of claim 1, wherein the dots have a contrast ratio of between about 0.1 and 0.6.

3. The cosmetic applicator of claim 1, wherein at least a portion of one surface of the applicator has an area of coverage of the cosmetic composition of from about 10 to 50%.

4. The cosmetic applicator of claim 3, wherein a first portion of the applicator has a first area of coverage and a second portion of the application has a second area of coverage, wherein the first area of coverage is greater than the second area of coverage.

5. The cosmetic applicator of claim 4, wherein the first area of coverage is at least 50% greater than the second area of coverage.

6. The cosmetic applicator of claim 4, wherein the second portion of the applicator circumscribes the first portion.

7. The cosmetic applicator of claim 1, wherein the substrate comprises a pliable foam material.

8. The cosmetic applicator of claim 7, wherein the applicator is shaped to conform to a periorbital region of a human face.

9. The composition of claim 8, wherein the release layer has a surface energy of between about 18 and 30 dynes/cm.

10. A cosmetic applicator for providing a natural looking cosmetic benefit, comprising:
    a. a substrate configured to support a transferable cosmetic composition; and
    b. a solid, transferable cosmetic composition disposed on the substrate as a multitude of dots arranged in a discontinuous stochastic pattern, wherein the cosmetic composition comprises a colorant and an adhesive and the composition provides a Color Improvement Value of at least about 1% and a delta-E value (ΔE) of less than about 10 when applied to a target skin surface comprising periorbital dyschromia,
    wherein the dots have a maximum dimension of between about 10 µm and 250 µm and a radius ratio of between 1 and 10,
    wherein the pattern of dots comprises a diffuse edge,
    wherein the substrate includes a release layer and the cosmetic composition is disposed on the release layer,
    wherein the colorant is a plurality of pigment particles dispersed in the adhesive, and
    wherein a ratio of pigment to adhesive in the composition is from about 1:10 to 1:1.

11. A method of improving the appearance of skin, comprising:
    a. identifying a target portion of discolored skin; and
    b. applying a solid, transferable cosmetic composition to the target portion of discolored skin using an applicator, the cosmetic composition comprising a colorant and an adhesive and the applicator comprising at least one substrate, wherein the cosmetic composition is disposed on the substrate as a multitude of dots arranged in a discontinuous stochastic pattern,
    wherein the dots have a maximum dimension of between about 10 µm and 250 µm and a radius ratio of between 1 and 10,
    wherein the pattern of dots comprises a diffuse edge,
    wherein the substrate includes a release layer and the cosmetic composition is disposed on the release layer,
    wherein the colorant is a plurality of pigment particles dispersed in the adhesive, and
    wherein a ratio of pigment to adhesive in the composition is from about 1:10 to 1:1.

12. The method of claim 11, wherein the target portion of discolored skin includes periorbital dyschromia and the cosmetic composition provides a Color Improvement Value of at least about 1%.

13. The method of claim 11, wherein the cosmetic composition provides a ΔE of less than about 10.

14. The method of claim 12, wherein the composition has an L* value of from about 30 to 80, a c* value of from about 10 to 50, and an h* value of from about 30 to 80.

* * * * *